(12) United States Patent
Smith et al.

(10) Patent No.: US 7,645,227 B2
(45) Date of Patent: Jan. 12, 2010

(54) IMPLANTS AND METHODS FOR PELVIC FLOOR REPAIR

(75) Inventors: Daniel J. Smith, Dayton, NJ (US); Allison London Brown, New Hope, PA (US); Peter Komarnycky, Lebanon, NJ (US); Robert A. Roda, Newtown, PA (US)

(73) Assignee: Ethicon, Inc., Somerville, NJ (US)

( * ) Notice: Subject to any disclaimer, the term of this patent is extended or adjusted under 35 U.S.C. 154(b) by 20 days.

(21) Appl. No.: 11/748,136

(22) Filed: May 14, 2007

(65) Prior Publication Data

US 2008/0287968 A1   Nov. 20, 2008

(51) Int. Cl.
*A61F 2/02* (2006.01)
(52) U.S. Cl. .................................................... 600/30
(58) Field of Classification Search ................ 600/30
See application file for complete search history.

(56) References Cited

U.S. PATENT DOCUMENTS

| | | | |
|---|---|---|---|
| 4,307,716 A | 12/1981 | Davis | |
| 5,922,026 A | 7/1999 | Chin | |
| 6,131,576 A | 10/2000 | Davis | |
| 6,216,353 B1 | 4/2001 | Schenck | |
| 6,216,698 B1 | 4/2001 | Regula | |
| 6,543,141 B1 | 4/2003 | Biehl | |
| 7,131,944 B2 * | 11/2006 | Jacquetin ..................... | 600/30 |
| 2002/0028980 A1 | 3/2002 | Thierfelder et al. | |
| 2002/0083949 A1 | 7/2002 | James | |
| 2004/0039453 A1 * | 2/2004 | Anderson et al. ........ | 623/23.72 |
| 2005/0016545 A1 | 1/2005 | Nissenkorn | |
| 2005/0277806 A1 | 12/2005 | Cristalli | |
| 2006/0058575 A1 | 3/2006 | Zaddem et al. | |
| 2006/0260618 A1 * | 11/2006 | Hodroff et al. ............... | 128/830 |

FOREIGN PATENT DOCUMENTS

| | | |
|---|---|---|
| DE | 3720858 A | 1/1989 |
| RU | 2209605 C2 | 7/2001 |
| WO | WO 01/06951 A1 | 2/2001 |

(Continued)

OTHER PUBLICATIONS

Samuelsson, E.C. et al. "Signs of genital prolapse in a Swedish population of women 20 to 59 years of age and possible related factors", Am. J. Obstet. Gynecol. 180:299-305 (1999).

(Continued)

*Primary Examiner*—John P Lacyk

(57) ABSTRACT

A pelvic floor implant including a central body portion having an anterior edge having a centrally located recess therein, a posterior edge having a centrally located tab, and first and second lateral side edges. First and second strap-like extension portions extend outwardly to first and second distal ends from first and second end regions of the posterior edge of the central body portion. The first and second strap-like extension portions extending outwardly at an angle so as to form a substantially "Y" shaped implant in combination with the central body portion. First and second pockets are located at the first and second distal ends of the first and second strap-like extensions respectively, each having a closed end substantially adjacent to the distal end of the strap-like extension, and having an open end proximal thereto and opening toward the central body portion.

16 Claims, 7 Drawing Sheets

FOREIGN PATENT DOCUMENTS

| WO | WO 02/078552 A1 | 10/2002 |
| WO | WO 02/078568 A1 | 10/2002 |
| WO | WO 03/028585 A2 | 4/2003 |
| WO | WO 03/073960 A | 9/2003 |
| WO | WO 2004/045457 A1 | 6/2004 |

OTHER PUBLICATIONS

Olsen, A.L. et al. "Epidemiology of Surgically Managed Pelvic Organ Prolapse and Urinary Incontinence", Obstet Gynecol vol. 89, No. 4, 501-506 (1997).

Winters, J.C. et al. "Abdominal Sacral Colpopexy and Abdominal Enterocele Repair in the Management of Vaginal Vault Prolapse", Urology 55-63 (2000).

Deval, B. et al., What's new in prolapse surgery? Current Opinion in Urology 13:315-323 (2003).

Maher, C.F. et al., "Abdominal sacral colpopexy or vaginal sacrospinous colpopexy for vaginal vault prolapse: A prospective randomizer study", Am. J. Obstet. Gynecol. 190:20-26 (2004).

Cervigni, M., et al., "The use of synthethics in the treatment of pelvic organ prolapse. Current Opinion in Urology" 11:429-435 (2001).

Visco, A.C., et al., "Vaginal mesh erosion after abdominal sacral colpopexy", Am. J. Obstet Gynecol. 184:297-302 (2001).

Boyles, S.H. et al., "Procedures for pelvic organ prolapse in the United States 1979-1997", American Journal of Obstetric Gynecology 188: 108-115 (2003).

Pang, Man-Wah, et al., "An overview of pelvic floor reconstructive surgery for pelvic organ prolapse", Journal of Paediatrics, Obstetrics and Gynaecology (2003).

* cited by examiner

IMPLANTS AND METHODS FOR PELVIC FLOOR REPAIR

BACKGROUND OF THE INVENTION

1. Field of the Invention

The present invention relates to implants suitable for use in repairing various pelvic floor prolapse conditions, and more particularly to meshes having particular application for anterior and/or posterior pelvic floor repair and methods for implanting the same.

2. Background Discussion

Each year in the USA approximately 200,000 women undergo pelvic organ prolapse surgery. Pelvic organ prolapse generally involves the descent of one or more of the uterus, the bladder or the rectum along the vagina towards (or in extreme cases protruding beyond) the introitus. Women of advancing years, or those that have borne several children are more frequent sufferers of pelvic organ prolapse. Traditional vaginal surgery to address these conditions is associated with a high failure rate of between 30-40%. Complex and elaborate abdominal, vaginal and laparoscopic procedures such as abdominal sacral colpopexy, transvaginal sacrospinous ligament fixation, and laparoscopic sacral colpopexy have been developed to reduce the risk of prolapse recurrence. Unfortunately these procedures require a high level of surgical expertise and are only available to a small number of specialist practitioners and therefore to a small number of patients. Details of various procedures currently in use are described in Boyles S H., Weber A M, Meyn L. "Procedures for pelvic organ prolapse in the United States", 1979-1997, American Journal of Obstetric Gynecology 2003, 188; 108-115.

Recently there has been a trend towards the use of reinforcing materials to support a vaginal wall damaged by prolapse. Prosthetic materials such as donor fascia lata, pig dermis and various types of synthetic mesh have been utilized with mixed success. These materials are generally positioned adjacent to or in contact with the vaginal wall or walls and sutured into position or secured via straps.

WO 2004/045457 discloses a different approach that utilizes a prosthetic material in repairing damaged pelvic tissue, and subsequently inserts an intra-vaginal splint. The splint is placed into the vagina, and operates to reduce the mobility of the vaginal walls during tissue ingrowth. The repairs are typically made by dissecting either the posterior wall of the vagina, the anterior wall of the vagina, or both. A graft of either synthetic material, such as a polypropylene mesh or other fabric, or autologous or analogous material is freely placed without fixation in the dissected area between the vaginal wall and the prolapsing organ. The vaginal incision is then closed by suture or other tissue closure means, at which time the vaginal splint is inserted into the vagina and affixed to both walls at the cervical cuff. The splint stabilizes the vagina, keeps it elongated in its anatomical position, and helps to hold the graft in place by preventing it from sliding or dislodging. Eventually the fascial tissue on each side of the graft will infiltrate into it thereby incorporating it into the body, and the splint can subsequently be removed.

The present invention provides an implant for use in procedures such as those described above, having a configuration and construction particularly suited for such applications.

SUMMARY OF THE INVENTION

An implant for pelvic floor repair is provided having a central body portion having an anterior edge, a posterior edge, and first and second lateral side edges. The anterior edge has a recess extending inwardly from the anterior edge and substantially centrally located along the anterior edge, and the posterior edge has a tab element extending outwardly from the posterior edge and substantially centrally located along the posterior edge. First and second strap-like extension portions extend outwardly to first and second distal ends from first and second end regions of the posterior edge of the central body portion. The first and second strap-like extension portions extending outwardly at an angle so as to form a substantially "Y" shaped implant in combination with the central body portion. First and second pockets are located at the first and second distal ends of the first and second strap-like extensions respectively. Each has a closed end substantially adjacent to the distal end of the strap-like extension, and an open end proximal thereto and opening toward the central body portion.

In one embodiment, the anterior edge has a length less than a length of the posterior edge. The implant may further be made of a non-absorbable, biocompatible material, and in one embodiment is made of polypropylene. In alternate embodiments, the implant is a mesh implant made of knitted filaments of polypropylene, or is made of a material selected from the group consisting of, an absorbable polymer, a non-absorbable polymer, and a natural material. It may further be made of a combination of absorbable and non-absorbable materials.

In yet another embodiment, the overall shape of the implant is suitable for both posterior and anterior repairs.

Also provided is an implant for pelvic floor repair including a central body portion having an anterior edge, a posterior edge, and first and second lateral side edges, and first and second strap-like extension portions extending outwardly to first and second distal ends from first and second end regions of the posterior edge of the central body portion. The first and second strap-like extension portions extend outwardly at an angle so as to form a substantially "Y" shaped implant in combination with the central body portion. First and second pockets are located at the first and second distal ends of the first and second strap-like extensions respectively, each having a closed end substantially adjacent to the distal end of the strap-like extension, and having an open end proximal thereto and opening toward the central body portion.

Also provided is a method for implanting an implant for pelvic floor repair including providing an implant having a central body portion having an anterior edge, a posterior edge, and first and second lateral side edges, first and second strap-like extension portions extending outwardly to first and second distal ends from first and second end regions of the posterior edge of the central body portion. The first and second strap-like extension portions extend outwardly at an angle so as to form a substantially "Y" shaped implant in combination with the central body portion. First and second pockets are located at the first and second distal ends of the first and second strap-like extensions respectively, with the first and second pockets each having a closed end substantially adjacent to the distal end of the strap-like extension, and having an open end proximal thereto and opening toward the central body portion. The method further includes inserting one end of an instrument in the first pocket of the implant, inserting the combination instrument and first pocket through an incision in a patient's vagina and to a location substantially adjacent to a pelvic side wall or sacrospinous ligament on a first side of the patient's body, removing the instrument from the first pocket and from the patient's body substantially without repositioning the first strap-like extension portion, inserting one end of an instrument in the second pocket of the implant, inserting the combination instrument having the second pocket through the incision and to a location substantially adjacent to the pelvic sidewall on an opposite side of the patient's body, and removing the instrument from the second pocket and from the patient's body substantially without repositioning the second strap-like extension portion.

In yet another embodiment, in the first and second inserting steps the combination instrument and first and second pockets are inserted to a location substantially adjacent the pelvic side wall on first and second sides of the patient's body respectively, and the method further includes positioning the central body portion of the implant between the patient's vagina and bladder, and closing the vaginal incision.

Finally, in yet another embodiment, in the first and second inserting steps the combination instrument and first and second pockets are inserted to a location substantially adjacent the sacrospinous ligament on first and second sides of the patient's body respectively, and the method further includes positioning the central body portion of the implant between the patient's vagina and rectum, and closing the vaginal incision.

DETAILED DESCRIPTION OF THE INVENTION

Figure 1:
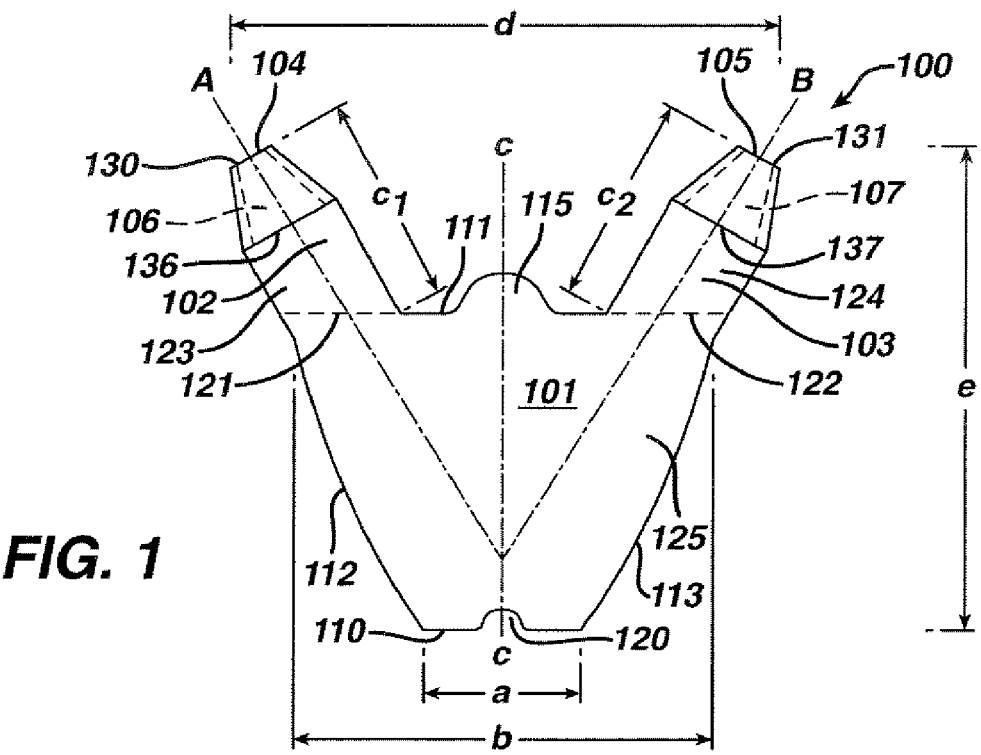
FIG. 1 is a top view illustrating an implant according to the present invention.

Referring now to FIG. 1, an implant 100 is provided having particular application for repair of anterior, posterior and/or apical vaginal defects. The implant may be comprised of any suitable biocompatible material, absorbable or non-absorbable, synthetic or natural or combination thereof. Preferably the implant is a mesh type material, and in a preferred embodiment, is constructed of knitted filaments of extruded polypropylene, such as that manufactured and sold by Ethicon, Inc. of Somerville, N.J. under the name GYNEMESH PS.

The implant 100 has a central body portion 101 having anterior and posterior edges 110, 111, and first and second lateral side edges 112, 113 that may be slightly arced as shown. The anterior edge 110 has a recess 120 extending inwardly therein and the posterior edge has a tab element 115 extending outwardly therefrom. The recess and tab element are both substantially centrally located along the anterior and posterior edges respectively as shown to aid in properly positioning the implant. In addition, the tab element 115 provides additional material for attachment to the uterus if desired. The central body portion is preferably sized and shaped to be positioned either between the urinary bladder and the upper ⅔ of the vagina, or between the rectum and the upper ⅔ of the vagina as will be described further below.

The implant further has first and second 102, 103 strap-like extension portions extending outwardly from the central body portion to first and second distal ends 104, 105. The strap-like extension portions extend outwardly from first and second end regions 121, 122 of the posterior edge 111 of the central body portion at an angle so as to substantially form a "Y" shaped implant in combination with the central body portion 101. In a preferred embodiment, lines A and B that substantially symmetrically bisect a top surface 123, 124 of the strap-like extension portions, and line C that substantially symmetrically bisects a top surface 125 of the central body portion, intersect within the central body portion as shown in FIG. 1.

Each of the first and second strap-like extension portions 102, 103 each further include a pocket 106, 107 at their respective distal ends. Each pocket has a closed end 130, 131 substantially adjacent to the distal ends 104, 105 of the strap-like extension portion, two closed sides, and an open end 136, 137 proximal of the closed end, with the open end opening toward the central body portion 101 as illustrated. Preferably, the first and second pockets and underlying strap-like extension taper inwardly from the open end to the closed end as shown in FIG. 1.

In a preferred embodiment, the anterior edge 110 has a length a of approximately 30 mm, and the posterior edge 111 has a length b of approximately 80 mm. Further, the strap-like extensions 102, 103 preferably have a length $c_1$, $c_2$ of approximately 40 mm, with the implant 100 having an overall width and length d, e of approximately 10.5 cm and 9 cm respectively.

Figure 2A:
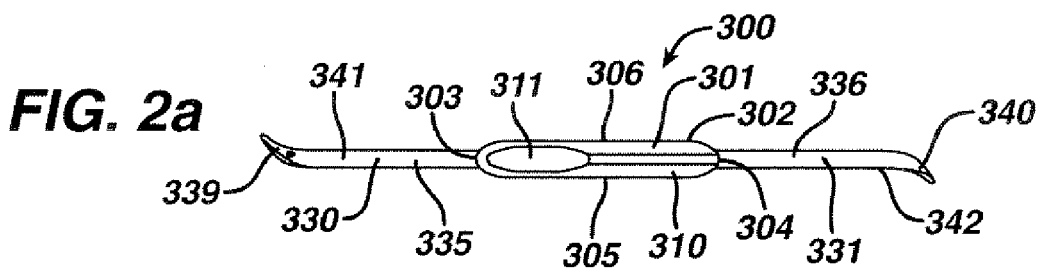
FIGS. 2a and 2b are top and side perspective views respectively of an instrument particularly suitable for aiding in implantation of the implant of FIG. 1.
Figure 2B:
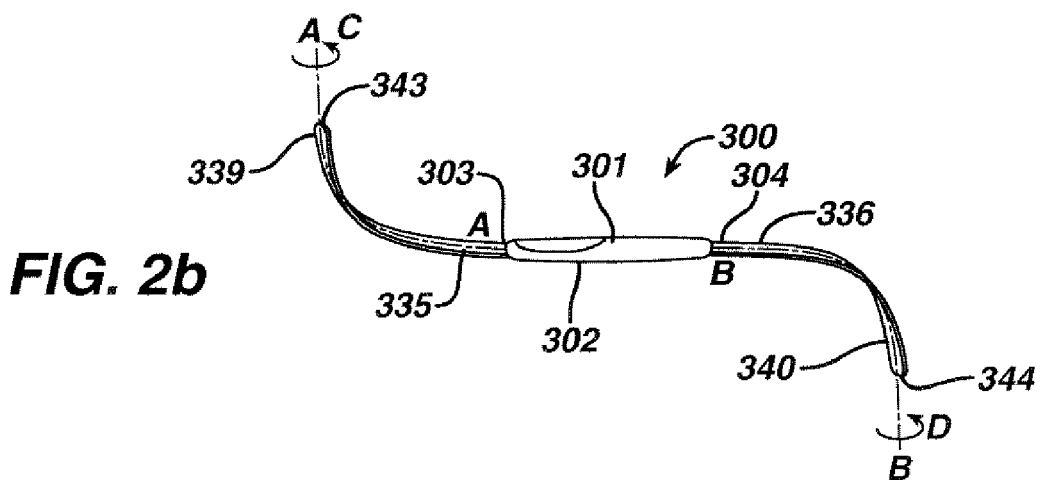

The open end of the pocket is capable of receiving the end of an implantation instrument or device to facilitate implantation of the implant as will be described further below. An implantation device particularly suited for implantation for an anterior repair is illustrated in FIGS. 2a-2b, which are top and side perspective views respectively. The instrument 300 includes a grip portion 310 suitably configured for gripping the instrument. The grip portion 310 has a top side 301, a bottom side 302, first and second end sides 303, 304, and front and rear sides 305, 306. The grip portion is preferably comprised of polycarbonate or any biocompatible plastic, and may include one or more grip regions 311 configured to received a users finger or thumb to facilitate handling of the instrument.

The instrument 300 further includes a first substantially rigid extension arm 330 extending laterally outward from the first end side 303 of the grip portion, and a second substantially rigid extension arm 331 extending laterally outward from the second end side 304 of the grip portion. The arms may be made of any suitable biocompatible material having sufficient stiffness for implantation procedures as described below, such as stainless steel. Although the first and second extension arms are described herein as extending outwardly from the first and second sides of the grip portion, it is to be understood that the first and second extension arms may be one unitary structure extending through the grip portion (i.e., a polymeric grip portion formed around a central portion of the unitary structure), and reference to "first and second" extension arms is not to be construed as requiring two separate extension arms separately secured to the grip portion although it could. Each of the first and second extension arms extend outwardly along first and second longitudinal axes, which for the purposes of the present application is defined as a line extending along the length of the extension arm and substantially centrally located relative to the cross-section of the extension arm, as shown by dotted lines A-A and B-B in FIG. 2b.

Each of the first and second extension arms further includes a substantially straight portion 335, 336 and a distal portion 339, 340. The substantially straight portions 335, 336 are proximal to the first and second 303, 304 end sides of the grip portion. Within the first and second substantially straight portions 335, 336, the extension arms lie substantially within a single first plane, and the same plane as one another. The distal portions 339, 340 extend from the substantially straight portions to first and second distal ends 343, 344 respectively. Within the first distal portion 339 of the first extension arm, the extension arm extends upwardly away from the first plane, and also rotates counterclockwise about longitudinal axis A-A as shown by arrow C in FIG. 2b. Within the distal portion 340 of the second extension arm, the extension arm extends downwardly away from the first plane, and also rotates counterclockwise about longitudinal axis B-B as shown by arrow D in FIG. 2b. Preferably, the first and second distal ends are blunt, with a substantially flat edge.

Figure 8:
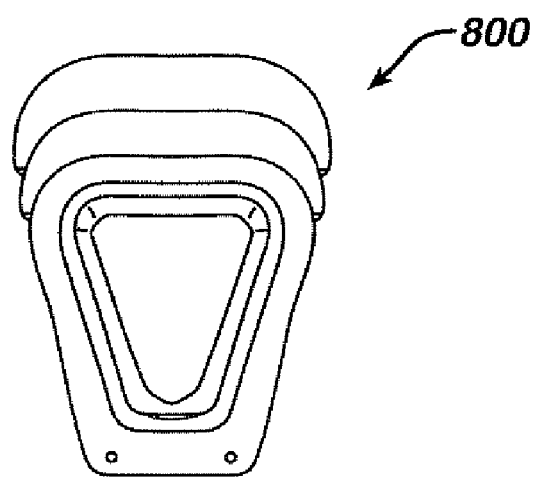

As indicated, the implant of the present invention is intended for use in various pelvic floor repair procedures, and may be used in connection with a intra-vaginal splint of the type described in detail in co-pending U.S. patent application Ser. Nos. 11/258,441, 11/334,966 and 10/534,930, the disclosures of which are incorporated herein by reference in their entirety, to aid in temporarily holding the implant in place during initial tissue ingrowth into the implant. One example of such a splint 800 is illustrated in FIG. 8. Exemplary procedures for implanting the implant will now be described in detail.

Figure 4A:
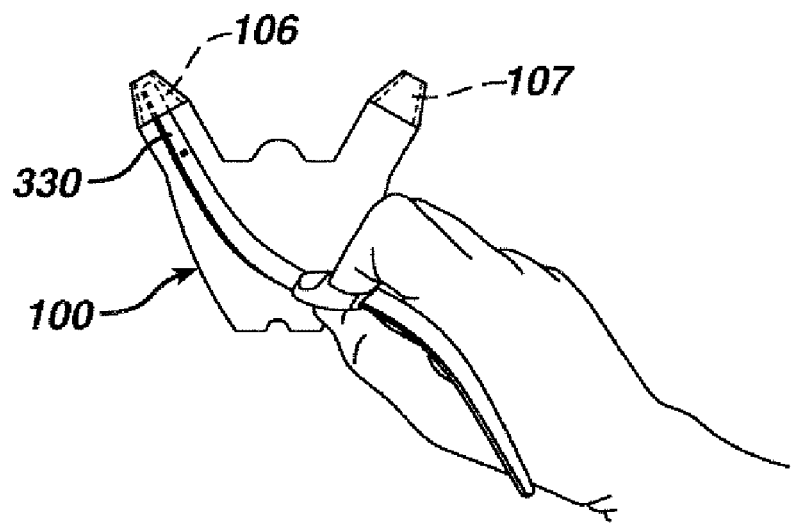
FIGS. 4a-4d illustrate various aspects of a method for implanting the implant of FIG. 1 for an anterior repair.
Figure 4B:
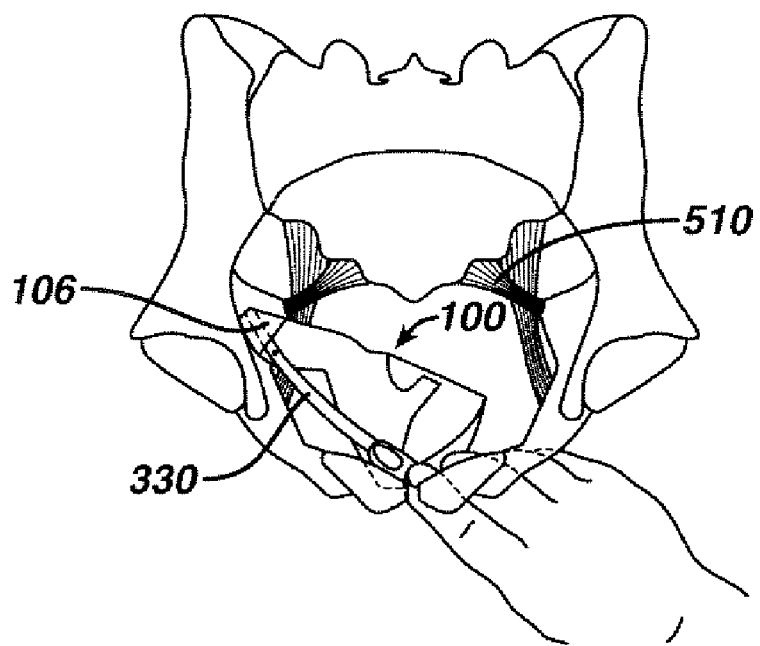

The implant as described and illustrated herein has particular application for repairing anterior, posterior, and/or apical vaginal defects. For an anterior repair when reinforcement of only the anterior vaginal wall is needed, the implant 100 is intended to be placed between the urinary bladder 500 and the upper ⅔ of the vagina 501 (see FIG. 4d), with the central body portion extending laterally approximately at the level of the arcus tendineus fascia pelvis (ATFP), the approximate position of which is illustrated by reference numeral 521 in FIG. 4c. The anterior vaginal epithelium is first dissected off the bladder, dissecting the full thickness of the vaginal wall and avoiding separation into two layers. The dissection is continued laterally toward the pelvic sidewall (also illustrated approximately by 521) and to the depth of the ischial spine 522. Further dissection is done to create channels for placement of the strap-like extensions 102, 103 of the implant 100, with the extensions preferably being placed flush against pelvic side wall and parietal fascia of the obturator internus muscle 523 (FIG. 4b). The dissection on each side should create a channel anterior and superior to the ischial spine and superficial to the ATFP, the obturator internus muscle, and parietal fascia.

Figure 3A:
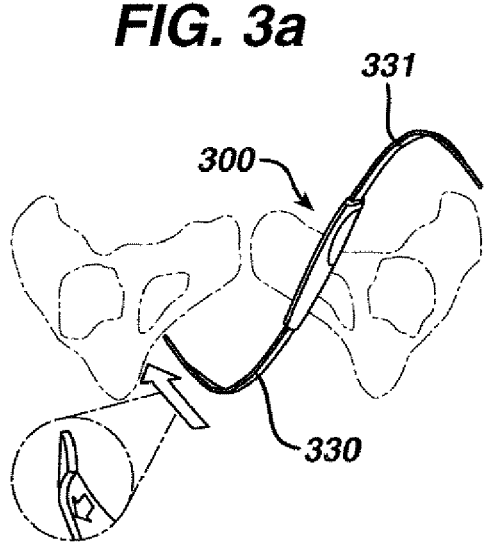
FIGS. 3a-3d illustration the orientation of the instrument of FIGS. 2a-2b when used to aid in implantation of the implant of FIG. 1.
Figure 3B:
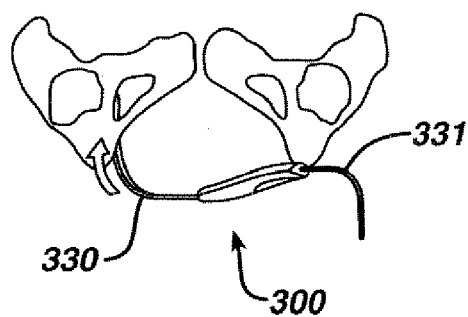
Figure 3C:
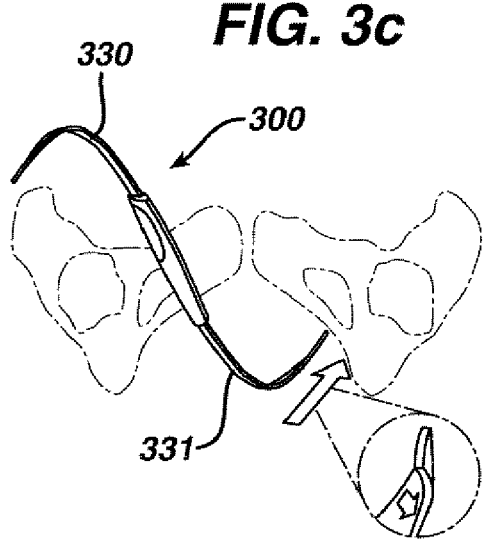
Figure 3D:
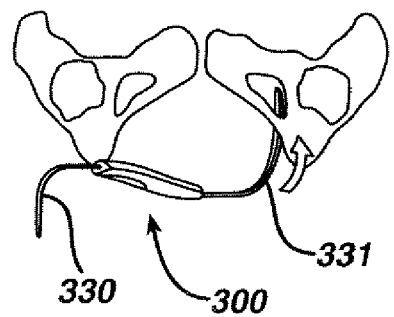
Figure 4C:
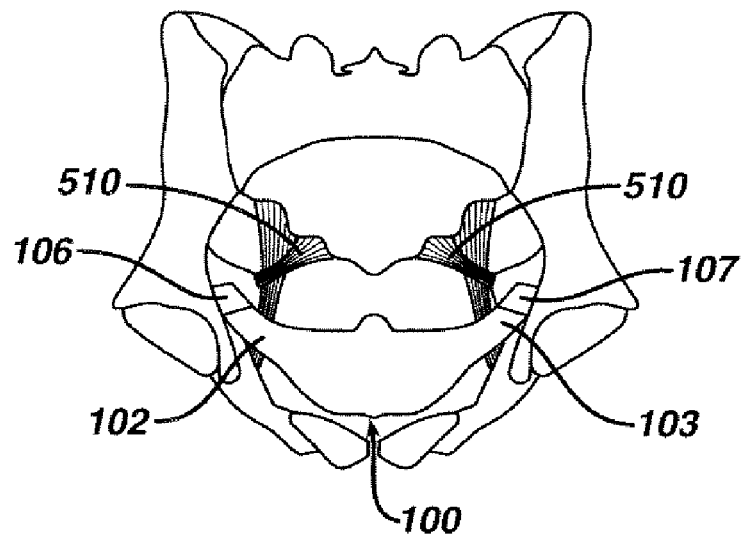
Figure 4D:
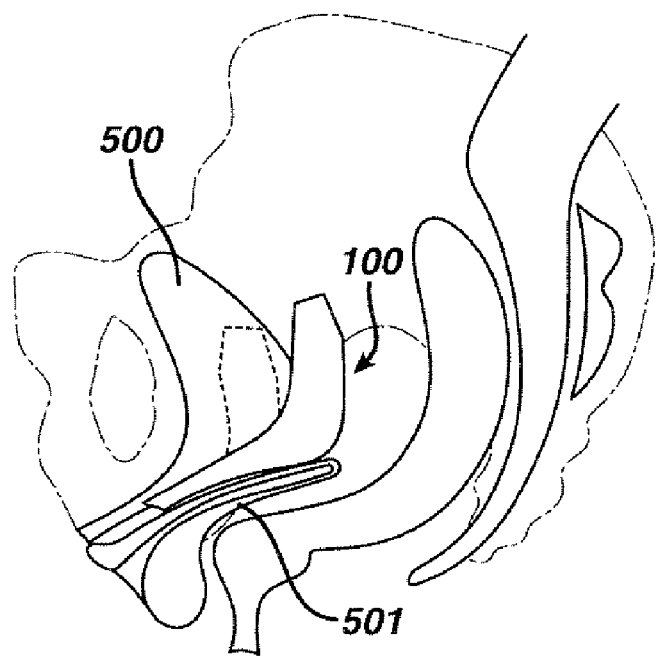

Following dissection, the implant 100 is placed over the pre-vesical tissue with the straps inserted into each right and left channel created by the dissection anterior and superior to the ischial spine as described above. Implantation of the mesh and strap-like extension portions may be facilitated by using the instrument 300 illustrated in FIGS. 2a-2b and described herein. As shown in FIG. 4a, the distal end 343 of the first extension arm 330 is inserted into the first pocket 106 of the implant, with the pocket facing upwards. Visual indicators 524, such as the arrows shown in FIGS. 3a and 3c, may be used to ensure proper orientation of the instrument. The instrument and implant is then inserted through the channel described above (as shown in FIG. 4b, which, for the purposes of clarity does not illustrate most tissue) on the right side of the patient's body until the grip portion 301 comes in contact with the labia majora on the contra-lateral side. The grip portion is then lowered until approximately parallel to the floor, such that the distal tip is adjacent to and in contact with the internus muscle. The instrument is then removed, and the distal end 344 of the second extension arm 331 inserted into the second pocket 107, with the combination inserted into the second channel formed on the left side of the patient's body. FIGS. 3a and 3b further illustrate positioning of the instrument 300 during implantation on the right side of the body. For illustrative clarity, neither the implant nor soft tissue structures are shown. FIGS. 3c and 3d similarly illustrate positioning of the instrument during implantation on the left side of the body. When the instrument is subsequently removed, the implant should be placed as illustrated in FIGS. 4c and 4d. The central body portion 101 of the implant is then positioned loosely over the underlying vaginal tissue. The vaginal epithelium is then closed in a suitable manner.

Figure 5A:
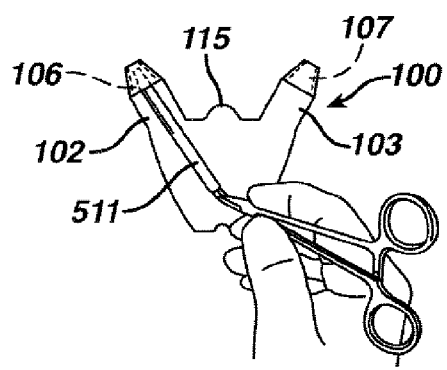
FIGS. 5a-5d illustrate various aspects of a method for implantation of the implant of FIG. 1 for a posterior repair.
Figure 5B:
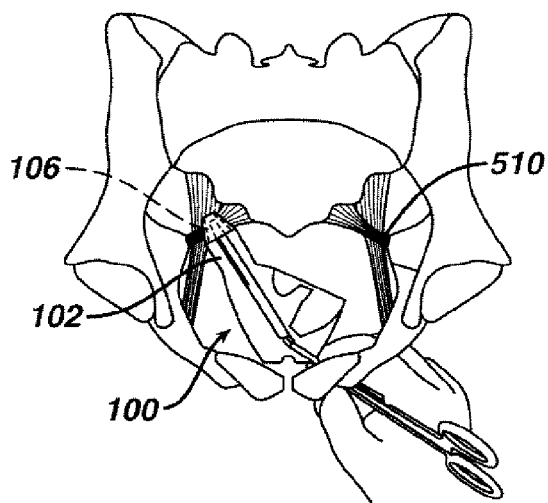
Figure 5C:
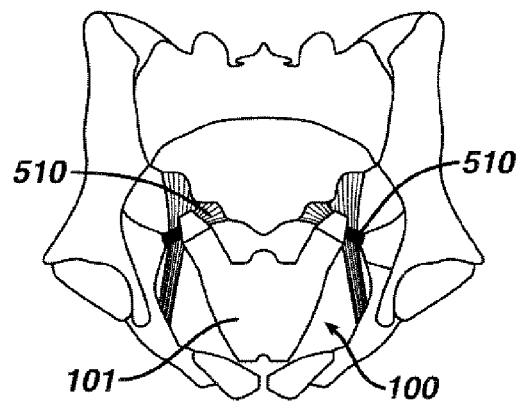
Figure 5D:
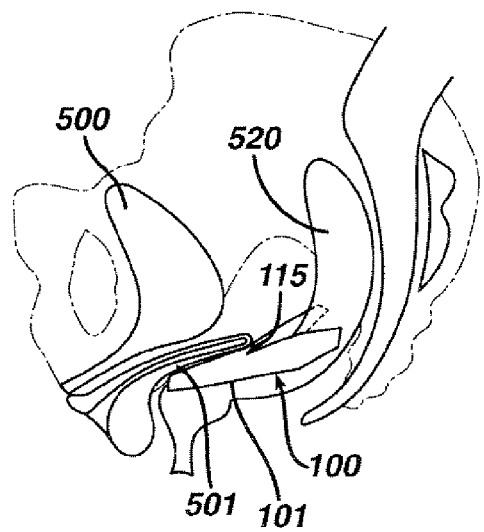

For a posterior repair (when reinforcement of only the posterior vaginal wall is needed), the full thickness of the posterior vaginal epithelium is first dissected off the pre-rectal tissue (rectum 520 illustrated in FIG. 5d). The dissection for the central body portion 101 is continued laterally on each side to the levator ani muscle at a depth to the level of the ischial spine, and then channels are created through each of the rectal pillars (not shown) and onto, but not through, each sacrospinous ligament 510. The dissected channels into which the strap-like extension portions of the implant are placed will ultimately help secure the implant after tissue ingrowth.

The implant is then placed over the pre-rectal tissue with the strap-like elements 102, 103 inserted into each right and left channel created by the dissection towards each sacrospinous ligament 510. The strap-like elements may be inserted with the aid of any suitable surgical instrument 511 (instrument 300 of the configuration shown in FIGS. 2a and 2b is not particularly suitable for posterior repair placement) one end of which is received within the pockets 106, 107 of the strip-like elements in a similar manner as described above. The ends of the strap-like elements are positioned so that they abut, but do not penetrate, the sacrospinous ligaments 510. Optionally, either before or after the insertion of the strap-like elements, the tab element 115 can be tacked (by suture or other fastener type element) to the apex of the vagina 501a as shown in FIG. 5d. Similarly, the implant may further be tacked down to pre-rectal tissue along the anterior edge. The centrally located tab element and recess help the surgeon to visually verify that the implant has been centrally aligned.

The central body 101 of the implant is then positioned loosely over the underlying vaginal fascia, and care is taken to ensure that the strap-like extensions are not folded or twisted. Depending on the vaginal dimensions, or the amount of lateral dissection, the central body may require trimming. The posterior vaginal wall epithelium is then closed over the implant, with final placement of the implant as illustrated in FIGS. 5c and 5d.

Figure 6A:
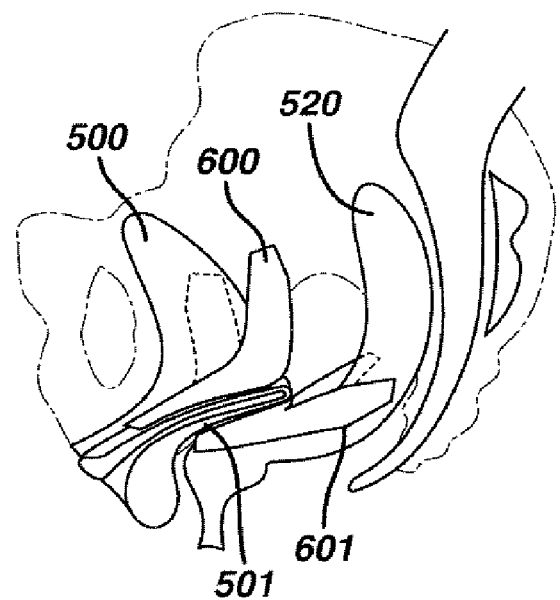
FIGS. 6a and 6b illustrate placement of two implants for a combination anterior/posterior repair.
Figure 6B:
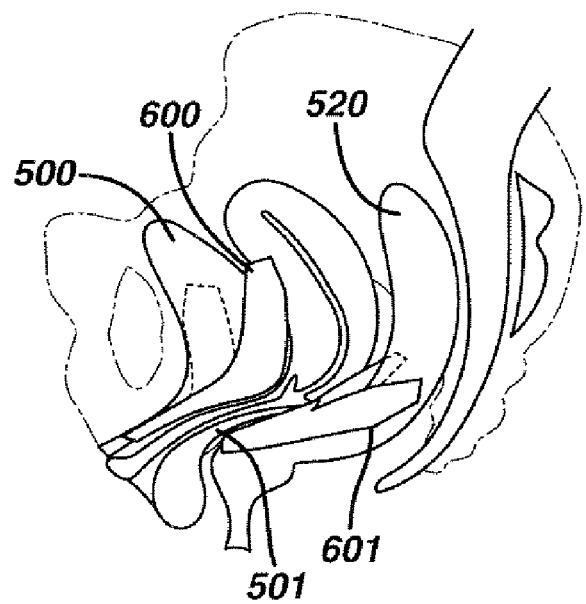
Figure 7:
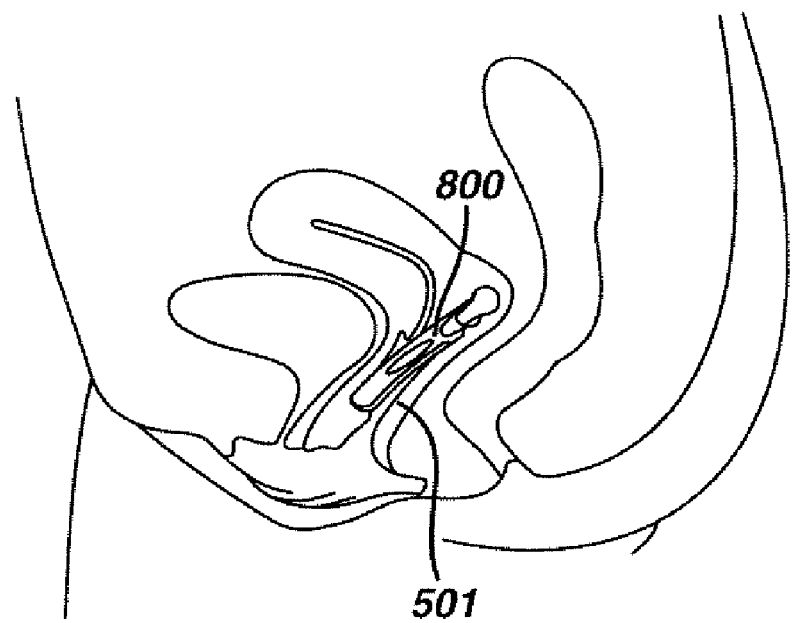
FIGS. 7 and 8 illustrate an exemplary vaginal splint and placement thereof that can be used in connection with the implants of the present invention.

If both anterior and posterior vaginal wall reinforcement is needed, two implants of the type described herein can be used, with the first 600 placed as described above for the anterior repair and the second placed 601 as described above for the posterior repair. The anterior repair should be performed first. Final placement of the first and second implants is shown in FIGS. 6a (hysterectomy) and 6b (no hysterectomy).

As indicated previously, the implants described above can be used in conjunction with a vaginal splint to aid in maintaining the proper positioning of the implants during initial tissue ingrowth. A splint 800, such as the exemplary splint shown in FIG. 8, is inserted into the vagina 501 as shown in FIG. 8, and as described in detail in co-pending U.S. application Ser. Nos. 11/258,441, 11/334,966 and 10/534,930, which have been incorporated herein by reference in their entirety. Following insertion the balloon is expanded, and the splint is left in place for approximately 1-2 days, after which it can be deflated. The splint can then remain in place for approximately 3-4 weeks to ensure that proper tissue ingrowth has occured.

It will be apparent from the foregoing that, while particular forms of the invention have been illustrated and described, various modifications can be made without departing from the spirit and scope of the invention. Accordingly, it is not intended that the invention be limited, except as by the appended claims.

What is claimed is:

1. An implant for pelvic floor repair comprising:
a central body portion having an anterior edge, a posterior edge, and first and second lateral side edges, wherein the anterior edge has a recess extending inwardly from the anterior edge and substantially centrally located along the anterior edge, and wherein the posterior edge has a tab element extending outwardly from the posterior edge and substantially centrally located along the posterior edge;
first and second strap-like extension portions extending outwardly to first and second distal ends from first and second end regions of the posterior edge of the central body portion, said first and second strap-like extension portions extending outwardly at an angle so as to form a substantially "Y" shaped implant in combination with the central body portion, and having a length,
first and second pockets located at the first and second distal ends of the first and second strap-like extensions respectively, the first and second pockets each having a closed end substantially adjacent to the distal end of the strap-like extension, and having an open end proximal thereto and opening toward the central body portion,
wherein the implant is sized and shaped to treat either an anterior pelvic floor defect or a posterior pelvic floor defect, but cannot treat both concurrently, and
wherein the length of the first and second strap-like extensions is such that when the implant is implanted between the bladder and the vagina to treat an anterior pelvic floor defect, the first and second distal ends may extend to a position substantially adjacent to, but cannot extend through, the obturator internus muscle, and when implanted between the vagina and rectum to treat a posterior pelvic floor defect, the first and second distal ends may extend to a position substantially adjacent to, but cannot extend through, the sacrospinous ligament.

2. The implant according to claim 1, wherein the anterior edge has a recess extending inwardly from the anterior edge and substantially centrally located along the anterior edge, and wherein the anterior edge has a length less than a length of the posterior edge, and wherein the posterior edge has a tab element extending outwardly from the posterior edge and substantially centrally located along the posterior edge.

3. The implant according to claim 1, wherein the implant is comprised of a non-absorbable, biocompatible material.

4. The implant according to claim 3, wherein the implant is comprised of polypropylene.

5. The implant according to claim 4, wherein the implant is a mesh implant comprised of knitted filaments of polypropylene.

6. The implant according to claim 1, wherein the implant is comprised of a material selected from the group consisting of, an absorbable polymer, a non-absorbable polymer, and a natural material.

7. The implant according to claim 1, wherein the implant is comprised of a combination of absorbable and non-absorbable materials.

8. The implant according to claim 1, wherein an overall shape of the implant is suitable for both posterior and anterior repairs.

9. An implant for pelvic floor repair comprising:
a central body portion having an anterior edge, a posterior edge, and first and second lateral side edges;
first and second strap-like extension portions extending outwardly to first and second distal ends from first and second end regions of the posterior edge of the central body portion, said first and second strap-like extension portions extending outwardly at an angle so as to form a substantially "Y" shaped implant in combination with the central body portion, and having a length,
first and second pockets located at the first and second distal ends of the first and second strap-like extensions respectively, the first and second pockets each having a closed end substantially adjacent to the distal end of the strap-like extension, and having an open end proximal thereto and opening toward the central body portion,
wherein the implant is sized and shaped to treat either an anterior pelvic floor defect or a posterior pelvic floor defect, but cannot treat both concurrently, and
wherein the length of the first and second strap-like extensions is such that when the implant is implanted between the bladder and the vagina to treat an anterior pelvic floor defect, the first and second distal ends may extend to a position substantially adjacent to, but cannot extend through, the obturator internus muscle, and when implanted between the vagina and rectum to treat a posterior pelvic floor defect, the first and second distal ends may extend to a position substantially adjacent to, but cannot extend through, the sacrospinous ligament.

10. The implant according to claim 9, wherein the anterior edge has a recess extending inwardly from the anterior edge and substantially centrally located along the anterior edge, and wherein the posterior edge has a tab element extending outwardly from the posterior edge and substantially centrally located along the posterior edge.

11. The implant according to claim 9, wherein the anterior edge has a length less than a length of the posterior edge.

12. The implant according to claim 9, wherein the implant is comprised of an absorbable or non-absorbable polymer, or a combination thereof.

13. The implant according to claim 9, wherein the implant is a mesh comprised of knitted filaments of polypropylene.

14. A method for implanting an implant for pelvic floor repair comprising:
providing an implant having a central body portion having an anterior edge, a posterior edge, and first and second lateral side edges, first and second strap-like extension portions extending outwardly to first and second distal ends from first and second end regions of the posterior edge of the central body portion, said first and second strap-like extension portions extending outwardly at an angle so as to form a substantially "Y" shaped implant in combination with the central body portion, and first and second pockets located at the first and second distal ends of the first and second strap-like extensions respectively, the first and second pockets each having a closed end substantially adjacent to the distal end of the strap-like extension, and having an open end proximal thereto and opening toward the central body portion;

inserting one end of an instrument in the first pocket of the implant;

inserting the combination instrument and first pocket through an incision in a patient's vagina and to a location substantially adjacent to but not through a pelvic side wall or sacrospinous ligament on a first side of the patient's body;

removing the instrument from the first pocket and from the patient's body substantially without repositioning the first strap-like extension portion;

inserting one end of an instrument in the second pocket of the implant;

inserting the combination instrument having the second pocket through the incision and to a location substantially adjacent to but not through the pelvic sidewall or sacrospinous ligament on an opposite side of the patient's body;

removing the instrument from the second pocket and from the patient's body substantially without repositioning the second strap-like extension portion, and leaving the implant within the patient without further securing the first and second strap-like extensions to the pelvic sidewall or sacrospinous ligament or other internal structure.

15. The method according to claim 14, wherein in the first and second inserting steps the combination instrument and first and second pockets are inserted to a location substantially adjacent the pelvic side wall on first and second sides of the patient's body respectively, and further comprising:

positioning the central body portion of the implant between the patient's vagina and bladder; and closing the vaginal incision.

16. The method according to claim 14, wherein in the first and second inserting steps the combination instrument and first and second pockets are inserted to a location substantially adjacent the sacrospinous ligament on first and second sides of the patient's body respectively, and further comprising:

positioning to central body portion of to implant between to patient's vagina and rectum; and closing the vaginal incision.

\* \* \* \* \*

UNITED STATES PATENT AND TRADEMARK OFFICE
CERTIFICATE OF CORRECTION

PATENT NO. : 7,645,227 B2  Page 1 of 1
APPLICATION NO. : 11/748136
DATED : January 12, 2010
INVENTOR(S) : Daniel J. Smith et al.

It is certified that error appears in the above-identified patent and that said Letters Patent is hereby corrected as shown below:

Col. 10, line 19 claim 15, change "to" second occurrence to --the--.
Col. 10, line 20 claim 16, line 20, change "to" to --the--.

Signed and Sealed this

Thirty-first Day of August, 2010

David J. Kappos
*Director of the United States Patent and Trademark Office*